United States Patent [19]

Cramm et al.

[11] 4,132,736
[45] Jan. 2, 1979

[54] PREPARATION OF 4-ALKYLTHIOSEMICARBAZIDES

[75] Inventors: Günther Cramm, Cologne; Eckart Kranz, Wuppertal; Günter Hellrung, Dormagen, all of Germany

[73] Assignee: Bayer Aktiengesellschaft, Leverkusen, Germany

[21] Appl. No.: 729,933

[22] Filed: Oct. 6, 1976

[30] Foreign Application Priority Data

Oct. 15, 1975 [DE] Fed. Rep. of Germany ........ 2546096

[51] Int. Cl.$^2$ ............................................ C07C 159/00
[52] U.S. Cl. ................................ 260/552 SC; 260/567
[58] Field of Search .................. 260/552 SC, 554, 567

[56] References Cited

U.S. PATENT DOCUMENTS

| 2,657,234 | 10/1953 | Klarer et al. ................. 260/552 SC |
| 3,539,587 | 11/1970 | Swakon ...................... 260/553 R X |
| 3,911,006 | 10/1975 | Hearsey et al. ................. 260/553 A |

FOREIGN PATENT DOCUMENTS

| 634690 | 1/1962 | Canada .............................. 260/553 A |
| 138018 | 8/1970 | Czechoslovakia. |
| 2013371 | 4/1970 | France .............................. 260/552 SC |
| 83559 | 8/1971 | German Democratic Rep. ..... 260/552 SC |

OTHER PUBLICATIONS

Smolik et al., CA 75: 140302y (1971).

PQM, S.A., CA 61: 14539g (1964).
Losanitch, J. Chem. Soc., 119, pp. 763-765 (1921).
Jensen et al., Acta Chem. Scand. 22, pp. 15-17 (1968).

*Primary Examiner*—Thomas Waltz
*Attorney, Agent, or Firm*—Sprung, Felfe, Horn, Lynch & Kramer

[57] ABSTRACT

4-Alkylthiosemicarbazides of the formula

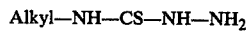

are produced by heating at about 40 to 90° C the novel hydrazinium salts of N-alkyldithiocarbamic acids of the formula

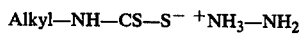

in a solvent while removing by-product $H_2S$ as by use of vacuum or passage of an inert gas through the reaction mixture, advantageously in the presence of a catalytic amount of sulfur to speed up the reaction. Hydrazine hydrate may also be present. The hydrazinium salt starting material can be prepared by reacting the corresponding alkylamine, ammonia, carbon disulfide and hydrazine, and the reaction solution directly employed in the heating step of the present invention without isolation of the intermediate.

10 Claims, No Drawings

PREPARATION OF 4-ALKYLTHIOSEMICARBAZIDES

The present invention relates to a new process for the preparation of known 4-alkyl-thio-semicarbazides, which can be used as intermediate products for the synthesis of plant protection agents and especially of herbicidal active compounds.

It has been disclosed by G. Pulvermacher in Chemische Berichte 26, 2812 (1893) and 27, 622 (1894) and by K. A. Jensen, U. Anthoni, B. Kagi, Ch. Larsen and C. Th. Pedersen in Acta. Chem. Scand. 22, 15 (1968), that 4-alkyl-thiosemicarbazides are obtained when alkyl isothiocyanates are reacted with hydrazine or hydrazine hydrate in the present of a solvent, i.e.

a) Alkyl—NCS + H$_2$N—NH$_2$.
(H$_2$O)→Alkyl—NH—CS—NH—NH$_2$

However, this process has the disadvantage that alkyl isothiocyanates, which are to be used as starting materials, are expensive and an economical design of the process is thus not possible.

Furthermore, it has been disclosed by K. A. Jensen, U. Anthoni, B. Kagi, Ch. Larsen and C. Th. Pedersen in Acta. Che. Scand. 22, 16 (1968) and Derwent CPI 66.231 S, Section E that 4-alkyl-thiosemicarbazides are obtained when N-alkyl-dithiocarbamate esters are reacted with hydrazine in the presence of a solvent, i.e.

b) Alkyl—NH—CS—S—Alkyl +
H$_2$H—NH$_2$→Alkyl—NH—CS—NH—NH-
1—Alkyl'—SH

This process also is uneconomical since the yields are only about 65% in some cases and, moreover, the elimination of the alkylmercaptans which are formed as by-products is very expensive.

In addition, it has been disclosed by K. A. Jensen, H. Anthoni, B. Kagi, Ch. Larsen and C. Th. Pedersen in Acta. Chem. Scand. 22, 17 (1968) and by R. S. Mc Elhinney in J. Chem. Soc. 1966, 950, that 4-alkyl-thiosemicarbazides are obtained when N-unsubstituted dithiocarbazate esters are reacted with primary amines, i.e.

c)
Alkyl'S—CS—NH—NH$_2$+Alkyl—NH$_2$→Alkyl—NH—CS—NH—NH$_2$—Alkyl'SH

This process also is not very economical since the yields are 40% and less and the elimination of mercaptans necessitates the use of special purification equipment.

Furthermore, it has been disclosed in German Patent Specification No. 832,891 that thiosemicarbazide and its alkyl, aryl, aralkyl and heterocyclic derivatives can be prepared when dithiocarbamates are reacted with hydrazine, i.e.

d) R—NH—CS—SM +
NH$_2$—NH$_2$→R—NH—CS—NH—NH$_2$—MHS

R = alkyl, aryl, aralkyl or a heterocyclic structure
M = ammonium or potassium

However, under the process conditions indicated in the cited specification, the alkyl compounds can be obtained only in extremely low yield (less than 1%). This has led K. A. Jensen, U. Anthoni, B. Kagi, Ch. Larsen and C. Th. Pedersen to state in Acta. Chem. Scand. 22, 17 (1968) that 4-alkyl-thiosemicarbazides (I) are not obtained when the hydrazinium salts of N-alkyl-dithiocarbamic acids are heated in solvents.

It has now been found that the known 4-alkyl-thiosemicarbazides of the formula (I)

Alkyl—NH—CS—NH—NH$_2$  (I)

are obtained when the hydrazinium salts of the corresponding N-alkyl-dithiocarbamic acids of the formula (II)

Alkyl—NH—CS—S$^-$ $^+$NH$_3$—NH$_2$  (II)

are heated, preferably to temperatures between about 60° and 80° C., in a solvent in the presence of sulfur, and optionally in the presence of hydrazine hydrate, under conditions which pull off H$_2$S and NH$_3$, e.g. reduced pressure or while passing an inert gas through the mixture. The hydrazinium salts of the formula (II), which are obtainable from the corresponding alkalamines, if necessary using ammonia as the base, and carbon disulfide and hydrazine, do not need to be isolated from the solution in which they are produced but rather can be directly employed in such solution in the instant reaction.

It is extremely surprising that, under the process conditions according to the invention, the 4-alkyl-thiosemicarbazides of the formula (I) are formed in good yield and high purity since, from Acta. Chem. Scand. 22, 17 (1968) it had to be expected that at most low conversions would take place.

The process according to the invention has a number of advantages. It proceeds with very good yields, can be carried out at low temperatures and requires as an auxiliary only catalytic amounts of sulfur. Moreover, the hydrazinium salts of the formula (II), which are to be used as starting materials, and also the corresponding (alkyl)-ammonium salts which are previously formed, do not need to be isolated but can be directly further reacted. In contrast to the known process variants, the process according to the invention is thus simpler and more economical. It proceeds without the formation of alkylmercaptans. The by-products formed during operation of the process, that is to say ammonia and hydrogen sulfide, are removed in a simple manner by carrying out the reaction according to the invention and are absorbed in scrubbers which, for example, are charged with sodium hydroxide solution or sulfuric acid. The 4-alkyl-thiosemicarbazides are obtained in good yield (> 80%) and in high purity. The same good yields are obtained when the hydrazinium salts are isolated at intervals.

If the hydrazinium salt of N-methyl-dithiocarbamic acid, which, for example, can be prepared from methylamine, ammonia, carbon disulfide and hydrazine and does not need to be isolated ("one pot process"), is used as the starting material, the course of the reaction can be represented by the following equations:

CH$_3$NH$_2$ + 2NH$_3$ + CS$_2$ ⟶ [CH$_3$NH—CS—S$^\ominus$ NH$_4^\oplus$]
①

① $\xrightarrow{NH_2-NH_2/H_2O}$ [CH$_3$NH—CS—S$^\ominus$ $^\oplus$NH$_3$—NH$_2$]
②

② 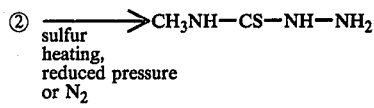

The hydrazinium salts to be used as starting materials are defined unambiguously by formula (II). In this formula, the alkyl radicals preferably have 1 to 4 carbon atoms and methyl is particularly preferred. These compounds have not been disclosed hitherto. They are obtained by reacting the ammonium or alkyl-ammonium salts of N-alkyl-dithiocarbamic acids of the formula (III)

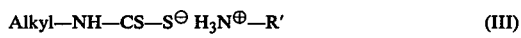

in which

R' is hydrogen or alkyl,
with hydrazine hydrate in the presence of a solvent, for example water, and optionally under reduced pressure, at temperatures between 20° and 90° C. The hydrazinium salts of the formula (II) are then either isolated by customary methods or directly further reacted in their reaction solution.

Ammonium and alkyl-ammonium salts of N-alkyl-dithiocarbamic acids of the formula (III) which are to be used as starting materials are disclosed in Chem. Abstr. 61, P 14539 h. They are obtained by reacting aqueous solutions of an alkylamine with ammonia or an alkylamine and carbon disulfide at temperatures of 0° to 25° C. They are either isolated by customary methods or further directly reacted in solution. The alkylamines to be used for this reaction are generally known and readily available substances. Examples which may be mentioned are: methylamine, ethylamine, n-propylamine, i-propylamine, n-butylamine, sec.-butylamine and tert.-butylamine.

Diluents which can be used for the process according to the invention are, preferably, water and other protic solvents, for example alcohols, such as ethanol and isopropanol, the formamides, such as dimethylformamide, and mixtures thereof.

The process according to the invention is carried out in the presence of sulfur as the catalyst and by this means the reaction times are considerably shortened. Hydrazine hydrate can also be added.

The process according to the invention is carried out at temperatures between about 40° and 90° C., preferably between about 60° and 80° C.

The process according to the invention is carried out while pulling off by-product gases, as by operating under reduced pressure or by passing an inert gas through the reaction mixture. In general, the reaction is carried out under pressures of between about 100 mm and 500 mm, preferably between about 300 mm and 400 mm, of Hg absolute, or nitrogen is preferably used as the inert gas.

When the process according to the invention is carried out, about 0.1–0.01 moles of sulfur, as the catalyst, and about 0.1–0.5 mole of hydrazine hydrate are employed per mole of the hydrazinium salt of the N-alkyl-dithiocarbamic acid of the formula (II). According to the special embodiment, that is to say when the hydrazinium salt and its precursor, that is to say the ammonium or alkylammonium salt of the formula (III), are not isolated, about 2 moles of aqueous ammonia solution and about 1 mole of carbon disulfide are employed per mole of alkylamine or about 1 mole of carbon disulfide is employed per 2 moles of alkylamine and subsequently about 1.1 to 1.5 moles of hydrazine hydrate in the presence of about 0.1 to 0.01 mole of sulfur are allowed to act on the reaction solution, the reaction being carried out either under reduced pressure or while passing an inert gas through the reaction mixture. Working up can be carried out either by concentrating the reaction solution, cooling to about 0° to 10° C. and filtering off the solid 4-alkyl-thiosemicarbazides of the formula (I) or by using the mother liquors and wash filtrates, which are obtained during the reaction, as the reaction medium in subsequent cycles and thus substantially preventing the losses in yield caused by the solubility.

The 4-alkyl-thiosemicarbazides of the formula (I) which can be prepared according to the process of the invention can be used as intermediate products for the synthesis of plant protection agents, especially of herbicidal active compounds as described in German Published Specifications DOS Nos. 1,670,925, 1,816,568, 1,901,672, 1,912,543, 2,028,778, 2,044,442 and 2,118,520.

The invention will be further described in the following illustrative examples wherein (a) and (b) show that the process employing sulfur as catalyst gives 4-methyl-thiosemicarbazide in a relatively short time (9–10 hours) and in good yields. If the reaction is carried out without sulfur as the catalyst, as in (c), 4-methyl-thiosemicarbazide is obtained in about 85% yield only after 15 hours.

EXAMPLE 1

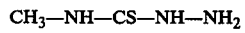

a) Using sulfur as the catalyst and nitrogen as the inert gas 76 g (1 mole) of carbon disulfide are added, at room temperature, to 100 g (1 mole) of an aqueous solution (31% strength) of methylamine and 125 g (2 moles) of aqueous ammonia (27.1% strength). After adding 3.2 g (0.1 mole) of sulfur and 60 g (1.2 moles) of hydrazine hydrate, the resulting dithiocarbamate solution is heated to 75° C. and nitrogen is blown through the mixture until the evolution of hydrogen sulfide has ceased (about 9 to 10 hours). Sulfur is deposited towards the end of the reaction and is filtered off hot. The thiosemicarbazide crystallizes out as the reaction solution cools. 88.5 g of 4-methyl-thiosemicarbazide, which has a melting point of 136°–138° C., are obtained.

b) Using sulfur as the catalyst and under reduced pressure 76 g (1 mole) of carbon disulfide are added, at room temperature, to 200 g (2 moles) of an aqueous solution (31% strength) of methylamine. After adding 3.2 g (0.1 mole) of sulfur and 60 g (1.2 moles) of hydrazine hydrate, the resulting dithiocarbamate solution is kept at a temperature of 75° to 80° C. and under a pressure of 400 mm until the evolution of hydrogen sulfide has ceased (about 9 to 10 hours). Sulfur is deposited towards the end of the reaction and is filtered off hot. The precipitate which is deposited on cooling is filtered off, washed with a little cold water and dried. 86.4 g of 4-methyl-thiosemicarbazide, which has a melting point of 136°–138° C., are obtained.

c) Without sulfur as the catalyst (=> prolonged reaction time) and under reduced pressure)

76 g (1 mole) of carbon disulfide are added, at room temperature, to 100 g (1 mole) of an aqueous solution (31% strength) of methylamine and 125 g (2 moles) of aqueous ammonia (27.1% strength). After adding 60 g (1.2 moles) of hydrazine hydrate, the resulting dithiocarbamate solution is heated to 80° C. under a pressure of 400 mm until the evolution of hydrogen sulfide has ceased, i.e. about 15 hours. The sulfur which has precipitated is filtered off hot and the product, which crystallizes out after concentrating the solution and cooling, is filtered off, washed with a little cold water and dried. 89.2 g of 4-methyl-thiosemicarbazide, which has a melting point of 135°–137° C., are obtained.

d) With isolation of the hydrazinium salts

After adding 50 g (1 mole) of hydrazine hydrate, the aqueous solution of 62 g (2 moles) of monomethylamine and 76 g (1 mole) of carbon disulfide is concentrated to half its volume at 30° to 40° C. under a water pump vacuum. The hydrazinium salt of N-methyl-dithiocarbamic acid crystallizes out. The precipitation can be completed by adding ethanol. The salt which has been filtered off is suspended in water and, after adding 10 g (0.2 mole) of hydrazine hydrate and 3.2 g (0.1 mole) of sulfur, is reacted further in accordance with variants (a) and (b).

e) Recycling of the mother liquor 137 g (1 mole) of the hydrazinium salt isolated in accordance with (d) are first reacted in water as described under (a) or (b); the mother liquors and washings thus obtained are then recycled for further reaction resulting in an increase in yield in such subsequent cycles.

The product of Example 1 is employed as follows to make the herbicidally active compound 3-(5-t-butyl-1,3,4-thiodiazol-2-yl)-1,3-dimethyl-urea according to German Published Specification DOS No. 2,118,520.

EXAMPLE 2 a) 160.5 g of phosphorus oxychloride are added slowly, at 90° C., to a solution of 91.6 g of N-methyl-thiosemicarbazide and 102.3 g of trimethylacetic acid in 400 ml of dioxane at such a rate that the reaction temperature remains in the range of 85° to 90° C. without the supply of heat. When the addition has been completed, the mixture is kept at 85° to 90° C. for several hours until the evolution of hydrogen chloride ceases and is then cooled and the supernatant liquid is decanted off from the solid mass in the reaction flask. The mass is comminuted and suspended in 700 ml of water and the suspension is rendered alkaline (pH value 8 to 9) by slowly adding sodium hydroxide tablets. The precipitate which has formed is filtered off, washed with water, dried in air and recrystallized from hexane. 119.4 g (80% of theory) of 2-methylamino-5-t-butyl-1,3,4-triadiazole, which has a melting point of 79°–81° C., are obtained.

162 g (2.85 moles) of methyl isocyanate are added dropwise in the course of one hour to a solution of 486.5 g (2.85 moles) of 2-methylamino-5-t-butyl-1,3,4-triadiazole in 1,700 ml of dioxane, while stirring, and during the addition the temperature rises to 50° to 55° C. After stirring for a further 1 to 2 hours, the suspension is cooled in ice and filtered and the filter residue is washed with hexane. 467 g (72% of theory) of 3-(5-t-butyl-1,3,4-thiadiazol-2-yl)-1,3-dimethylurea, which has a melting point of 162°–164° C., are obtained.

It will be appreciated that the instant specification and examples are set forth by way of illustration and not limitation, and that various modifications and changes may be made without departing from the spirit and scope of the present invention.

What is claimed is:

1. A process for the preparation of a 4-alkylthiosemicarbazide of the formula

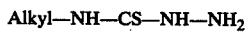

which comprises heating the hydrazinium salt of a N-alkyldithiocarbamic acid of the formula

in a solvent at a temperature of about 40° to 90° C. sufficiently to produce the 4-alkylthiosemicarbazide while removing by-product $H_2S$ by carrying out the reaction under sub-atmospheric pressure of 100 to 500 mm Hg or by passing an inert gas through the reaction mixture.

2. The process according to claim 1, wherein the heating is at a temperature of about 60° to 80° C. and is carried out in the presence of about 0.01 to 0.1 mole of sulfur per mole of hydrazinium salt.

3. The process according to claim 2, wherein the heating is carried out under a pressure of about 100 to 500 mm Hg.

4. The process according to claim 3, wherein the heating is carried out under a pressure of about 300 to 400 mm Hg.

5. The process according to claim 2, wherein heating is carried out while nitrogen is passed through the reaction mixture.

6. The process according to claim 1, wherein heating is carried out in the presence of hydrazine hydrate.

7. The process according to claim 2, wherein heating is carried out in the presence of about 0.1 to 0.5 mole of hydrazine hydrate per mole of hydrazinium salt.

8. The process according to claim 1, wherein the hydrazinium salt is prepared by reacting the corresponding alkylamine, ammonia, carbon disulfide and hydrazine, and without isolation of the hydrazinium salt the reaction solution is directly heated.

9. The process according to claim 8, wherein about 1 mole of carbon disulfide is used for every 2 moles of the alkylamine.

10. The process according to claim 9, wherein Alkyl is methyl, heating is at a temperature of about 60° to 80° C. in the presence of about 0.01 to 0.1 mole of sulfur per mole of hydrazinium salt.

* * * * *